United States Patent [19]
McBeth

[11] Patent Number: 5,117,841
[45] Date of Patent: Jun. 2, 1992

[54] CONDOM KEEPER AND KIT

[76] Inventor: Charles R. McBeth, 780 Promenade Twr., Richardson, Tex. 75080

[21] Appl. No.: 697,115

[22] Filed: May 8, 1991

Related U.S. Application Data

[63] Continuation-in-part of Ser. No. 462,771, Jan. 10, 1990, abandoned.

[51] Int. Cl.$^5$ .................................................. A61F 6/00
[52] U.S. Cl. ........................................ 128/844; 206/69
[58] Field of Search ................ 229/70, 77, 78 A, 920; 40/124; 128/844, 847, 918; 206/69, 38

[56] References Cited

U.S. PATENT DOCUMENTS

| | | | |
|---|---|---|---|
| 2,008,875 | 7/1935 | Peterson et al. | 206/69 |
| 2,087,780 | 7/1937 | Powell | 206/69 |
| 2,332,857 | 10/1943 | Karg | 206/69 |
| 3,207,421 | 9/1965 | Hunger et al. | 40/124 |
| 3,325,084 | 6/1967 | Ausnit | 229/77 |
| 3,991,497 | 11/1976 | Owens et al. | 40/124 X |
| 4,738,390 | 4/1988 | Brennan | 229/77 |
| 4,741,434 | 5/1988 | Liebman | 206/69 X |
| 4,781,288 | 11/1988 | Wing | 206/69 X |
| 4,805,820 | 2/1989 | Kearney et al. | 206/69 X |
| 4,874,092 | 10/1989 | Lara | 229/77 X |
| 4,892,188 | 1/1990 | Meadows | 206/69 X |

FOREIGN PATENT DOCUMENTS

| | | | |
|---|---|---|---|
| 635459 | 11/1963 | Belgium | 229/77 |
| 213080 | 11/1908 | Fed. Rep. of Germany | 229/77 |
| 823318 | 3/1951 | Fed. Rep. of Germany | 206/69 |
| 442835 | 2/1936 | United Kingdom | 206/69 |

*Primary Examiner*—Robert A. Hafer
*Assistant Examiner*—Sam Rimell
*Attorney, Agent, or Firm*—Ross, Howison, Clapp & Korn

[57] ABSTRACT

A condom keeper is provided that comprises an optically opaque receptacle portion having an opening adapted to receive at least one individually packaged condom, a cover portion adapted to cover the opening in the receptacle portion after the individually packaged condom is received therein without overlapping the rolled portion of the condom within the package, and resealable means for releasably securing the cover portion over the opening in the receptacle portion to permit repeated use with other individually packaged condoms. Kits are also provided that comprise the condom keeper of the invention in combination an individually packaged condom, and with packaging means further comprising a quantity of individually packaged condoms that is greater than the quantity of individually packaged condoms which can be inserted into the condom keeper.

7 Claims, 2 Drawing Sheets

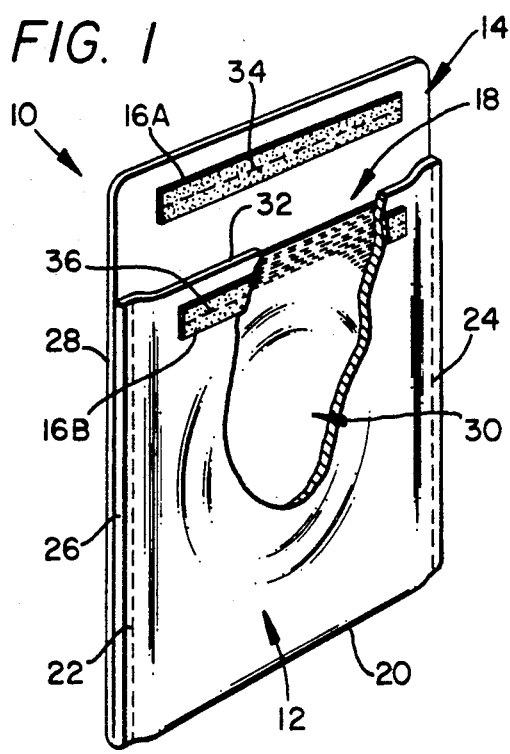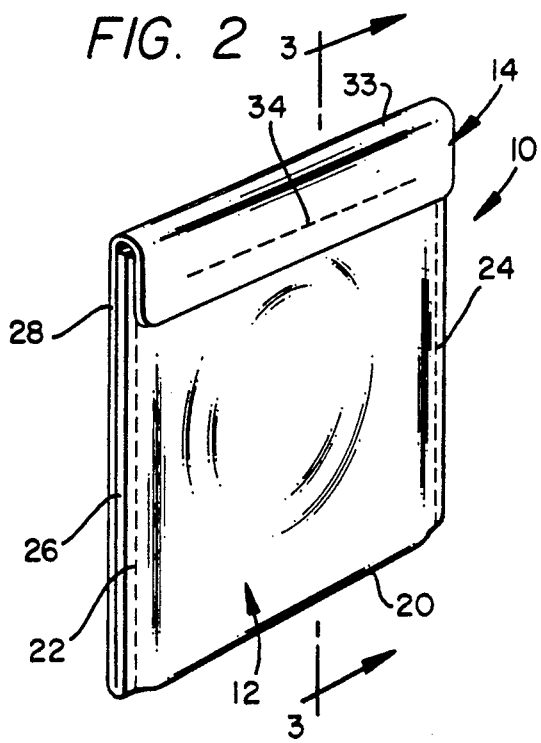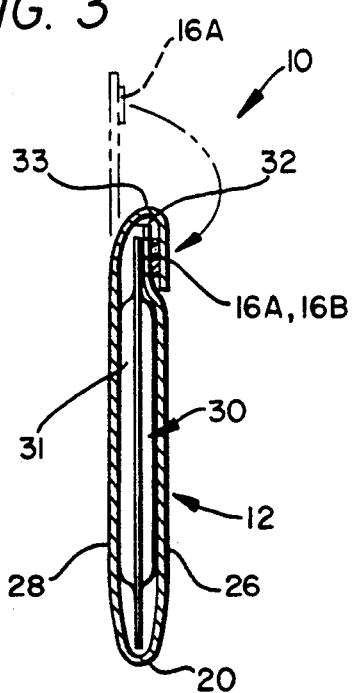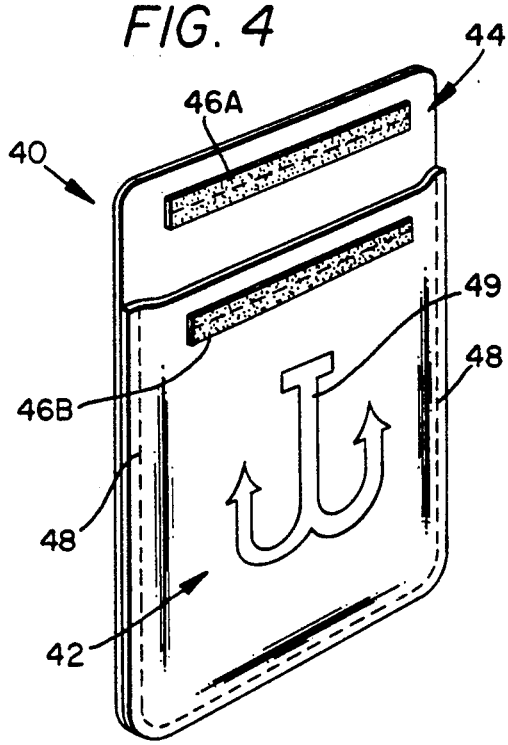

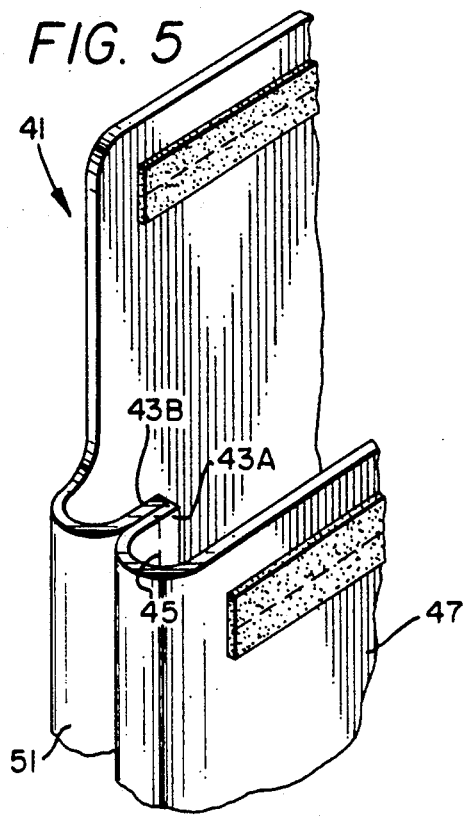
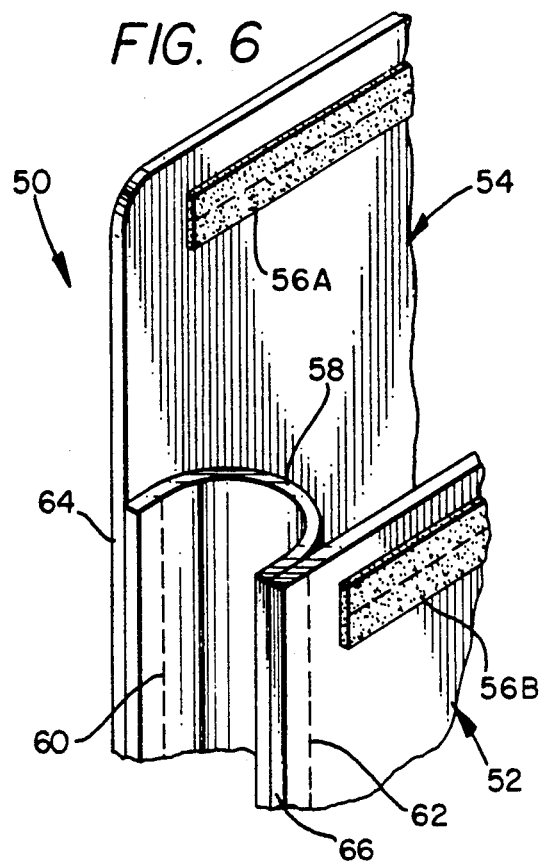
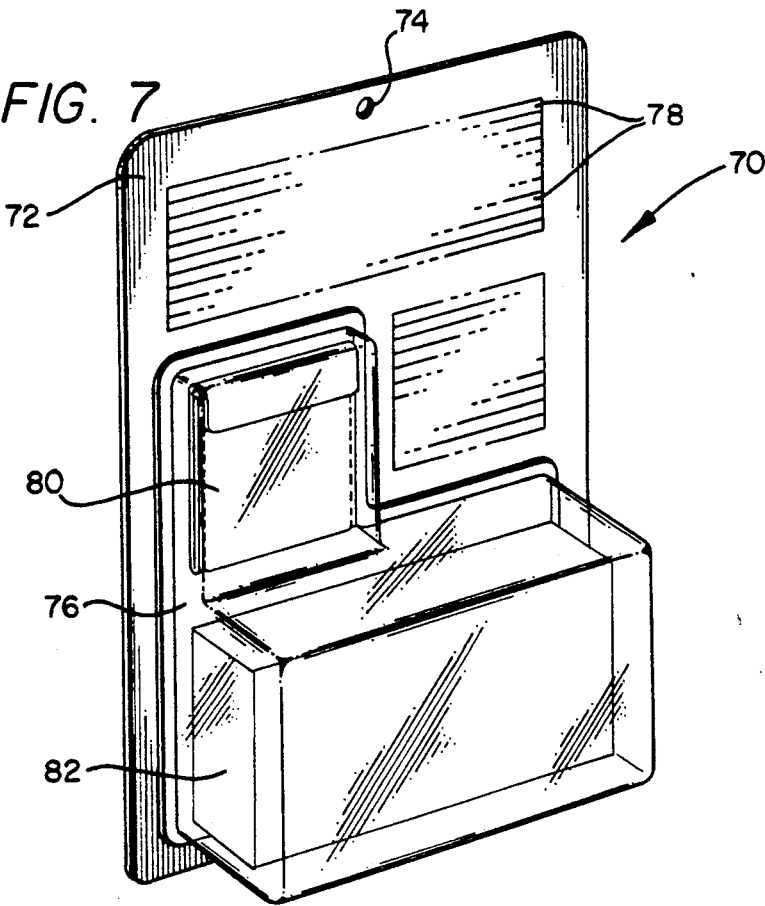

CONDOM KEEPER AND KIT

CROSS-REFERENCE TO RELATED APPLICATIONS

This application is a continuation in part of U.S. Ser. No. 07/462,771 filed Jan. 10, 1990, now abandoned.

BACKGROUND OF THE INVENTION

1. Technical Field

This invention relates to condoms, and more particularly, to means for protecting and discreetly carrying condoms prior to use. One aspect of the invention relates to a kit comprising at least one hermetically sealed condom together with means for protecting, carrying and/or storing the condom prior to use.

2. Background Of The Invention

There are various contraceptives available today, but condoms are the most highly recommended prophylactic. The Surgeon General, various public health organizations, colleges and high schools recommend the use of condoms and even advocate free distribution to some degree as a remedy to the current spread of AIDS and venereal disease. However, there is some embarrassment associated with carrying condoms, especially if they fall out of one's wallet, pocket or purse at an inopportune time (as depicted on at least one episode of virtually every television sit-com in the last five years, or in the movie, "Broadcast News" when purses had to be inspected by the Secret Service to gain entrance to an embassy party). There has been a long-felt need for a small, sealable pouch in which one or more foil-sealed condoms could be carried or stored to not only protect them against abrasion, but alleviate the anxiety that a condom might be evidenced under most embarrassing circumstances, thereby removing the reason that they aren't handy when needed. Such pouch with one condom should be small enough to place in a wallet without adding much bulk, but flexible enough to contain multiple condoms for carrying or storing elsewhere. It should have a releasable, secure, resealable, flexible closure. While the primary utility of the pouch is to facilitate carrying condoms on the person, there has also been a long-felt need for such a product in which to store condoms in an automobile or a suitcase or discreetly within reach from one's bed.

Although substantially impermeable to air and moisture, the materials used to package individual condoms are generally thin and lightweight, and the packages must be adapted to be torn open by the application of light-to-moderate manual force. Because of this fact, such packages are also susceptible to tearing or puncturing when placed in contact with other articles, such as might occur, for example, when individually packaged condoms are carried or maintained in a pocket, wallet, purse, glove compartment, desk drawer, or the like. Such tearing or puncturing may not be readily apparent to the user, but may be sufficient to permit contamination or degradation of the condom prior to use, or even failure of the condom during use at a subsequent time. One may also lose confidence in the reliability of a condom that has been carried for some time due to the worn or tattered appearance of the package in which it is wrapped, resulting in further anxiety and/or greater potential risk in the event of sexual contact.

The foregoing problems have deterred the effective utilization of condoms in the past, much to the detriment of the general public health. To obviate these problems, means are needed that can hold a single individually packaged condom, or a relatively small number of individually packaged condoms, that will protect the individually packaged condoms prior to use, and that will conceal individually packaged condoms to alleviate embarrassment to an individual carrying the condoms, or to a bystander.

SUMMARY OF THE INVENTION

According to one embodiment of the present invention, means are provided for holding and covering at least one conventional, individually packaged condom that will protect and conceal the packaged condom while it is carried on the person or stored by the consumer subsequent to purchase but prior to use.

According to another embodiment of the invention, means are provided for holding and covering a small number of conventional, individually packaged condoms in a convenient holder that will protect and conceal the packaged condoms while they are carried on the person or stored by the consumer subsequent to purchase but prior to use.

According to a preferred embodiment of the invention, the subject condom keeper comprises a receptacle portion adapted to receive at least one individually packaged condom, and a cover portion adapted to be releasably secured over the opening to the receptacle portion without overlapping the condom or condoms disposed inside the receptacle portion, thereby minimizing the overall thickness of the condom keeper.

According to another embodiment of the invention, means are provided for protecting and concealing individually packaged condoms, which means comprise a receptacle portion having an opening adapted to receive at least one individually packaged condom, a cover portion adapted to cover the opening in the receptacle portion after the individually packaged condom is received therein, and resealable means for releasably securing the cover portion over the opening in the receptacle portion to permit repeated use of the subject invention for the intended purpose with successive, individually packaged condoms over a prolonged period. According to a particularly preferred embodiment of the invention, the receptacle portion and the cover portion of the subject means are opaque and devoid of markings that would make the contents of the subject invention apparent if visible to a bystander while the cover portion is releasably secured to the receptacle portion with at least one individually packaged condom disposed therein.

According to another embodiment of the invention, a kit is provided that comprises at least one individually packaged condom in combination with the condom keeper of the invention.

According to another embodiment of the invention, a kit is provided that comprises a plurality of individually packaged condoms in combination with means for holding and concealing a small number of the individually packaged condoms, which means is adapted to protect and conceal the packaged condoms while the condoms are carried on the person or stored by the consumer subsequent to purchase and prior to use.

BRIEF DESCRIPTION OF THE DRAWINGS

The apparatus of the invention is further described and explained in relation to the following figures of the drawings in which:

3

FIG. 1 is a perspective view of a preferred embodiment of the invention having an individually packaged condom (depicted in phantom outline) disposed therein, in which the cover portion is not yet secured over the opening in the receptacle portion;

FIG. 2 is a perspective view of the preferred condom keeper of FIG. 1 wherein the cover portion has been releasably secured over the opening in the receptacle portion;

FIG. 3 is a sectional elevation view taken along line 3—3 of FIG. 2;

FIG. 4 is a perspective view of an alternate embodiment of the subject invention;

FIG. 5 is a detail perspective view, partially broken away, depicting another alternate embodiment of the subject invention;

FIG. 6 is a detail perspective view, partially broken away, depicting an alternate embodiment of the invention in which an optional side panel is incorporated into the receptacle portion to facilitate use of the invention with a plurality of individually packaged condoms; and FIG. 7 is a perspective view depicting a preferred kit of the invention, comprising a plurality of individually packaged condoms in combination with a preferred condom keeper of the invention.

Like numerals are used to indicate like parts in all figures of the drawings.

DESCRIPTION OF THE PREFERRED EMBODIMENTS

Referring to FIGS. 1 through 3, condom keeper 10 of the invention preferably comprises receptacle portion 12, cover portion 14, and means 16A, 16B for releasably securing cover portion 14 over opening 18 in receptacle portion 12. According to the preferred embodiment of the invention as shown in FIGS. 1 through 3, receptacle portion 12 and cover portion 14 are desirably constructed from a single piece of material folded along bottom edge 20 and secured by oppositely disposed rows of stitching 22, 24 at each side thereof.

The material utilized for receptacle portion 12 and cover portion 14 is preferably an optically opaque, flexible sheet material sufficiently thin and workable to be easily folded and stitched, but sufficiently thick and tough to withstand rubbing and wear (such as might occur when carried in a pocket, wallet, purse, glove compartment or the like) without rupturing, puncturing or tearing. Sheet material satisfactory for use in constructing receptacle portion 12 and cover portion 14 of condom keeper 10 is preferably selected from the group consisting of vinyl or another similarly satisfactory flexible sheet material, or leather, or any suitably heavy fabric.

Rows of stitching 22, 24 are preferably constructed with a conventional sewing machine utilizing standard, commercially available thread having strength and wearability commensurate with the strength and wearability of the sheet material employed in making the invention.

Alternatively, other means such as adhesives, heat sealing, sonic welding, or the like can be utilized for permanently securing face 26 to rear 28 of receptacle portion 12, depending upon the particular sheet material selected.

The interior dimensions of receptacle portion 12 are preferably slightly greater than the overall dimensions of a conventional, commercially available, hermetically sealed package comprising an individual condom. As shown in FIG. 1, which is partially broken away for illustrative purposes, individual condom package 30 is fully insertable into receptacle portion 12 of condom keeper 10 through opening 18 along top edge 32 of receptacle portion 12. Although condom keeper 10 is depicted in FIGS. 1-3 as containing a single, individually packaged condom, it will be appreciated that condom keeper 10 can be adapted to accommodate two or three individually packaged condoms by making receptacle portion 12 large enough to enclose the volume occupied by two or three such condoms.

As shown in FIGS. 1 through 3, cover portion 14, an extension of rear 28 of receptacle portion 12, is preferably adapted to be folded over top edge 32 of face 26, obscuring individual condom package 30 from view. According to a preferred embodiment of the invention, cover portion 14 does not extend downward over top edge 32 sufficiently to overlap the toroidally rolled portion 31 of the condom disposed in condom package 30, thereby minimizing the overall thickness of condom keeper 10. This is particularly desirable where condom keeper 10 is carried on the person in a wallet or pocket.

According to a preferred embodiment of the invention, a Velcro closure means comprising hook portion 16A and loop portion 16B is utilized for releasably securing cover portion 14 over face 26 of receptacle portion 12. It is understood, however, that the hook and loop portions of the closure can be reversed if desired, and that other similarly effective resealable closure means such as snaps, hooks, tongue and groove closures, or the like, can also be substituted for the Velcro closures depicted in simplified form in FIGS. 1 and 3-6 of the drawings.

As shown in FIG. 1, hook portion 16A is preferably secured by stitches 34 to the surface of cover portion 14 that is in facing contact with face 26 when cover portion 14 is folded over receptacle portion 12. Loop portion 16B is similarly attached to the outwardly facing surface of face 26 by stitches 36, although it will be appreciated that other means such as commercially available adhesives can also be used to secure the closure means to receptacle portion 12 and cover portion 14 of condom keeper 10.

Other preferred embodiments of the subject invention are shown and described in relation to FIG. 4. Condom keeper 40 comprises a front piece 42 that overlies and is secured to back piece 44 by stitches 48 or other similarly effective means. Front piece 42 and that portion of back piece 44 coextensive with front piece 42 cooperate to define a receptacle portion such as receptacle portion 12 previously discussed in relation to FIGS. 1 and 2. That portion of back piece 44 which extends beyond front piece 42 can likewise be folded over the top edge of front piece 42 and releasably secured by resealable closure means 46A, 46B. This method of construction is particularly preferred when it is desired to use a different material in front piece 42 than in back piece 44.

Also shown in FIG. 4 is graphic design element 49 on the outwardly facing surface of front piece 42. Graphic design element 49 preferably comprises any drawing, design, emblem, insignia, or other logo or combination of letters or figures that is not readily identifiable with condoms or their use, thereby promoting the objective of disguising or concealing the nature of the article or articles carried in the condom keepers of the invention. If desired, logos such as college, club or military insignias, mascots, or the like can be used as graphic design element 49 where appropriate. Graphic design element 49 can be applied to condom keeper 40 by any method suitable for use with the particular material utilized in making front piece 42, such as, for example, by printing, embossing, monogramming, or the like.

Referring to FIG. 5, a partial detail view of another embodiment of the invention is shown wherein condom keeper 41 is made by securing edges 43A, 43B together such as by stitches 45 while front face 47 and rear surface 51 are disposed in facing contact with each other, and then turning the joined pieces inside-out to place them in the position shown in FIG. 5.

Referring to FIG. 6, a partial detail view of yet another embodiment of the invention is shown wherein condom keeper 50 is particularly adapted to accommodate a plurality, preferably two or three, of individually packaged condoms. Condom keeper 50 comprises front piece 52 and back piece 54 having expandable web portion 58 disposed therebetween. Web portion 58 is secured to edge 66 of front piece 52 by stitches 62 and to edge 64 of back piece 54 by stitches 60. In this embodiment of the invention, back piece 54 should extend sufficiently above front piece 52 enable resealable closure members 56A, 56B to be brought into facing and contacting engagement. Although only a portion of condom keeper 50 is shown in FIG. 6, it is understood that web portion 58 desirably extends peripherally around the sides and bottom of the receptacle portion defined by front piece 52 and the coextensive portion of back piece 54. Where the condom keeper is made utilizing a single piece of material for front piece 52 and back piece 54, it is understood that one web 58 will be used on each side of condom keeper 50, and sufficient material will be provided in the bottom fold to allow room in the receptacle portion for the bottoms of the plurality of individually packaged condoms.

According to one preferred embodiment of the invention, a kit is provided that comprises a condom keeper as shown in FIGS. 1-3, 4, 5 or 6 in combination with at least one individually packaged, hermetically sealed condom.

Another preferred embodiment of the subject invention is disclosed in relation to FIG. 7, which depicts kit 70 comprising at least one condom keeper as previously disclosed herein in combination with a packaging means comprising a quantity of individually packaged condoms that is greater than the quantity of individually packaged condoms that can be held in such condom keeper at one time. Referring to FIG. 7, condom keeper 80 and box 82, which contains a quantity of individually packaged condoms greater than condom keeper 80 can receive at one time, are provided in combination inside transparent blister 76 attached to display card 72. Display card 72 further comprises aperture 74 for use in suspending kit 70 from a display rack in a retail establishment, with graphics 78 (shown in simplified, nonspecific form for purposes of illustration) as desired.

While the kit of the invention is depicted in a form preferred for use in marketing the inventive combination of elements disclosed herein, it will be appreciated that other forms of display or presentation can be similarly used within the scope of the invention.

Other alterations or modifications of the condom keeper and kit disclosed herein will likewise become apparent to those of ordinary skill in the art upon reading this disclosure, and it is intended that the scope of the invention be limited only by the broadest interpretation of the appended claims to which the inventor is legally entitled.

I claim:

1. A condom keeper kit comprising at least one prepackaged condom and a condom keeper, the condom keeper being made from an optically opaque, foldable and stitchable, flexible sheet material, said condom keeper further comprising: a receptacle portion adapted to receive and conceal each such prepackaged condom, said receptacle portion having an interior length and width slightly greater than that of a prepackaged condom, and an opening at one end thereof for receiving each said prepackaged condom; and a cover portion adapted to cover the opening in the receptacle portion after at least one such prepackaged condom is inserted therein without overlapping such condom, and resealable means for releasably securing the cover portion over the opening the receptacle portion.

2. The condom keeper kit of claim 1, wherein the receptacle portion further comprises an expandable web portion.

3. The condom keeper kit of claim 1, further comprising a graphic design element unrelated to condoms or their method of use.

4. A condom keeper kit comprising at least one hermetically sealed package containing a rolled condom, and a condom keeper, the condom keeper comprising an optically opaque, flexible vinyl receptacle portion having an opening at one end thereof adapted to receive at least one hermetically sealed package comprising a rolled condom and having a periphery substantially coextensive with but slightly larger than said package, a cover portion adapted to be folded over the opening in the receptacle portion after at least one such package is inserted therein without overlapping such condom, and resealable means for releasably securing the cover portion over the opening in the receptacle portion.

5. The condom keeper kit of claim 4, wherein the receptacle portion further comprises an expandable web portion.

6. The condom keeper kit of claim 4, wherein said condom keeper further comprises a graphic design element unrelated to said condoms or the method of use of said condom.

7. The combination of:
 a condom keeper kit further comprising an individually packaged condom and an optically opaque, foldable and stitchable receptacle portion having an opening at one end thereof adapted to receive at least one individually packaged condom, the receptacle portion being adapted to conceal said individually packaged condom and having a periphery substantially coextensive with but slightly larger than said individually packaged condom, a flexible cover portion adapted to cover the opening in the end of the receptacle portion without overlapping the individually packaged condom, and resealable means for releasably securing the cover portion over the opening in the receptacle portion;
 a plurality of individually packaged condoms; and
 packaging means adapted to receive and display said condom keeper kit and said plurality of individually packaged condoms, said packaging means comprising a display card and a transparent blister attached to the display card.

* * * * *